United States Patent [19]
Pletcher

[11] Patent Number: 5,669,973
[45] Date of Patent: Sep. 23, 1997

[54] APPARATUS FOR ELECTROSTATICALLY DEPOSITING AND RETAINING MATERIALS UPON A SUBSTRATE

[75] Inventor: Timothy Allen Pletcher, Eastampton, N.J.

[73] Assignee: David Sarnoff Research Center, Inc., Princeton, N.J.

[21] Appl. No.: 467,647

[22] Filed: Jun. 6, 1995

[51] Int. Cl.$^6$ ............................................. B05B 5/10
[52] U.S. Cl. .................. 118/624; 118/625; 118/696; 118/698; 128/203.15; 128/203.23; 604/58
[58] Field of Search ...................... 118/696, 698, 118/621, 624, 625, 628; 128/203.15, 203.23; 604/58

[56] References Cited

U.S. PATENT DOCUMENTS

| | | | |
|---|---|---|---|
| Re. 30,401 | 9/1980 | White | 204/192 N |
| 2,408,143 | 9/1946 | Huebner | 118/625 |
| 3,831,606 | 8/1974 | Damani | 128/266 |
| 3,971,377 | 7/1976 | Damani | 128/266 |
| 4,047,525 | 9/1977 | Kulessa et al. | 128/208 |
| 4,160,257 | 7/1979 | Carrish | 346/159 |
| 4,197,289 | 4/1980 | Sturzenegger et al. | 424/21 |
| 4,538,163 | 8/1985 | Sheridon | 346/155 |
| 4,570,630 | 2/1986 | Elliott et al. | 128/203.15 |
| 4,627,432 | 12/1986 | Newell et al. | 128/203.15 |
| 4,628,227 | 12/1986 | Briere | 315/111.81 |
| 4,664,107 | 5/1987 | Wass | 128/200.23 |
| 4,811,731 | 3/1989 | Newell et al. | 128/203.15 |
| 4,889,114 | 12/1989 | Kladders | 128/203.15 |
| 4,918,468 | 4/1990 | Miekka et al. | 346/159 |
| 4,992,807 | 2/1991 | Thomson | 346/155 |
| 5,014,076 | 5/1991 | Caley, Jr. et al. | 346/159 |
| 5,027,136 | 6/1991 | Fotland et al. | 346/159 |
| 5,031,610 | 7/1991 | Armstrong et al. | 128/200.23 |
| 5,115,803 | 5/1992 | Sioutas | 128/200.23 |
| 5,161,524 | 11/1992 | Evans | 128/203.15 |
| 5,176,132 | 1/1993 | Drought et al. | 128/203.15 |
| 5,186,164 | 2/1993 | Raghuprasad | 128/200.14 |
| 5,239,993 | 8/1993 | Evans | 128/203.15 |
| 5,243,970 | 9/1993 | Ambrosio et al. | 128/203.15 |
| 5,263,475 | 11/1993 | Altermatt et al. | 128/203.15 |
| 5,278,588 | 1/1994 | Kubelik | 346/259 |
| 5,301,666 | 4/1994 | Lerk et al. | 128/203.15 |
| 5,327,883 | 7/1994 | Williams et al. | 128/203.12 |
| 5,328,539 | 7/1994 | Sato | 156/275.5 |

FOREIGN PATENT DOCUMENTS

| | | |
|---|---|---|
| WO 93/0983 | 5/1993 | WIPO . |
| WO 94/08552 | 4/1994 | WIPO . |
| WO 94/13271 | 6/1994 | WIPO . |
| WO 94/23772 | 10/1994 | WIPO . |
| WO 95/00127 | 1/1995 | WIPO . |

*Primary Examiner*—Jill Warden
*Assistant Examiner*—Jan M. Ludlow
*Attorney, Agent, or Firm*—William J. Burke

[57] ABSTRACT

Apparatus having a substrate having a planar conductive plating located on a first surface of a dielectric layer and having a conductive trace (a collection trace) located on a second surface of the dielectric layer such that the conducting plating and the conductive trace have a parallel, spaced-apart relation. The conductive trace is charged by supplying a voltage to the plating and the trace to establish a voltage differential across the dielectric layer. As such, depending upon the magnitude of the voltage, polarity of the voltage and the duration for which the voltage is applied to the trace, a certain quantity and polarity of charge accumulates on the trace. The material to be deposited is charged to an opposite polarity than that of the trace and then the deposition material is applied to the trace. Consequently, the substrate electrostatically retains the deposition material on the collection trace.

22 Claims, 4 Drawing Sheets

APPARATUS FOR ELECTROSTATICALLY DEPOSITING AND RETAINING MATERIALS UPON A SUBSTRATE

The invention relates to electrostatic material deposition techniques and, more particularly, to a substrate containing electrodes that provide electrostatic fields for retention of various materials upon the substrate.

BACKGROUND OF THE DISCLOSURE

Electrostatic deposition of materials such as toner powders is typically accomplished using an ion gun or print head to deposit a charge pattern upon a dielectric substrate. In operation, the print head scans a dielectric substrate and selectively deposits on the substrate a pattern of charge. The charge pattern is then exposed to a cloud of oppositely charged powder particles and the charge pattern attracts the powder to the substrate. The powder adheres to the substrate via electrostatic forces between the charged substrate and the oppositely charged powder. If the powder, for example, is a printing toner, then the substrate (e.g., paper) is developed using heat to melt the toner powder such that the print pattern permanently adheres to the substrate.

As discussed above, such prior art material deposition systems use a print head that is separate from the substrate. The systems mechanically scan the head over the substrate to produce an accurate charge pattern. Such mechanical scanning requires a complicated head scanning mechanism. Such a mechanism is generally required where the pattern is constantly changing from one printing job to the next, e.g., systems that print text or graphics. However, other printing applications require repeated deposition of a particular charge quantity in a predefined pattern. Such an application includes retention of powdered drugs (medicament) at predefined locations on a substrate that is a component of a medication inhaler. Another such application is a printing stamp requiring a repeated pattern to be generated with each use of the stamp. Although in both of these applications, an identical charge pattern is repeatedly deposited on a substrate, the use of a prior art print head that robotically scans the substrate and deposits charge thereupon requires costly robotics.

Therefore, a need exists in the art for a material deposition technique that deposits and retains a deposition material directly upon the substrate without the use of a print head to generate a charge pattern.

SUMMARY OF THE INVENTION

The present invention overcomes the disadvantages associated with the prior art. Specifically, the present invention is a substrate having a planar conductive plating located on a first surface of a dielectric layer and having a conductive trace (a collection trace) located on a second surface of the dielectric layer such that the conductive plating and the conductive trace have a parallel, spaced-apart relation with respect to one another. The conductive trace is charged by supplying a voltage to both the plating and the trace to establish a voltage differential across the dielectric layer. As such, depending upon the magnitude of the voltage, polarity of the voltage and the duration for which the voltage is applied to the trace, a particular quantity and polarity of charge accumulates on the trace.

The material to be deposited is charged to an opposite polarity than that of the trace and then the deposition material is applied to the trace. Typically, if the deposition material is a powder, such as a powdered medicament, the powder is charged in a tribo-electric charging gun. If the material is a liquid, such as an ink, the liquid is charged using corona discharge apparatus within a liquid atomizer. In either case, the charged material is disposed over the charged collection trace and is electrostatically attracted to the trace. As such, the material adheres to the trace. The quantity of material adhered is directly proportional to the charge on the trace and the charge-to-mass ratio of the particles of deposition material. By determining the charge accumulated on the trace and the charge-to-mass ratio, a specific and repeatable quantity of deposition material is retained by the substrate.

The present invention provides a cost effective apparatus for repeatedly generating a well-defined charge pattern without using a robotically scanned print head. Applications for such apparatus include a substrate for retaining dry powder drugs within a drug inhaler and a substrate for retaining ink or toner in a programmable printing stamp.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

The present invention is apparatus for electrostatically retaining a deposition material upon a substrate. In general, the apparatus contains a conductive plate, a dielectric layer located upon the plate, and a conductive trace located upon the dielectric layer in a parallel spaced-apart relation with respect to the conductive plate. In use, a voltage is temporarily applied between the plate and the trace to charge the trace. Thereafter, deposition material, having a charge opposite that of the charge on the trace, is disposed upon the charged trace. The charged deposition material is attracted to the charged trace and is electrostatically adhered thereto. As such, the apparatus utilizes a relatively simple technique for electrostatically retaining the deposition material without using a mechanically scanned print head to form a charge pattern on the substrate.

Figure 1:
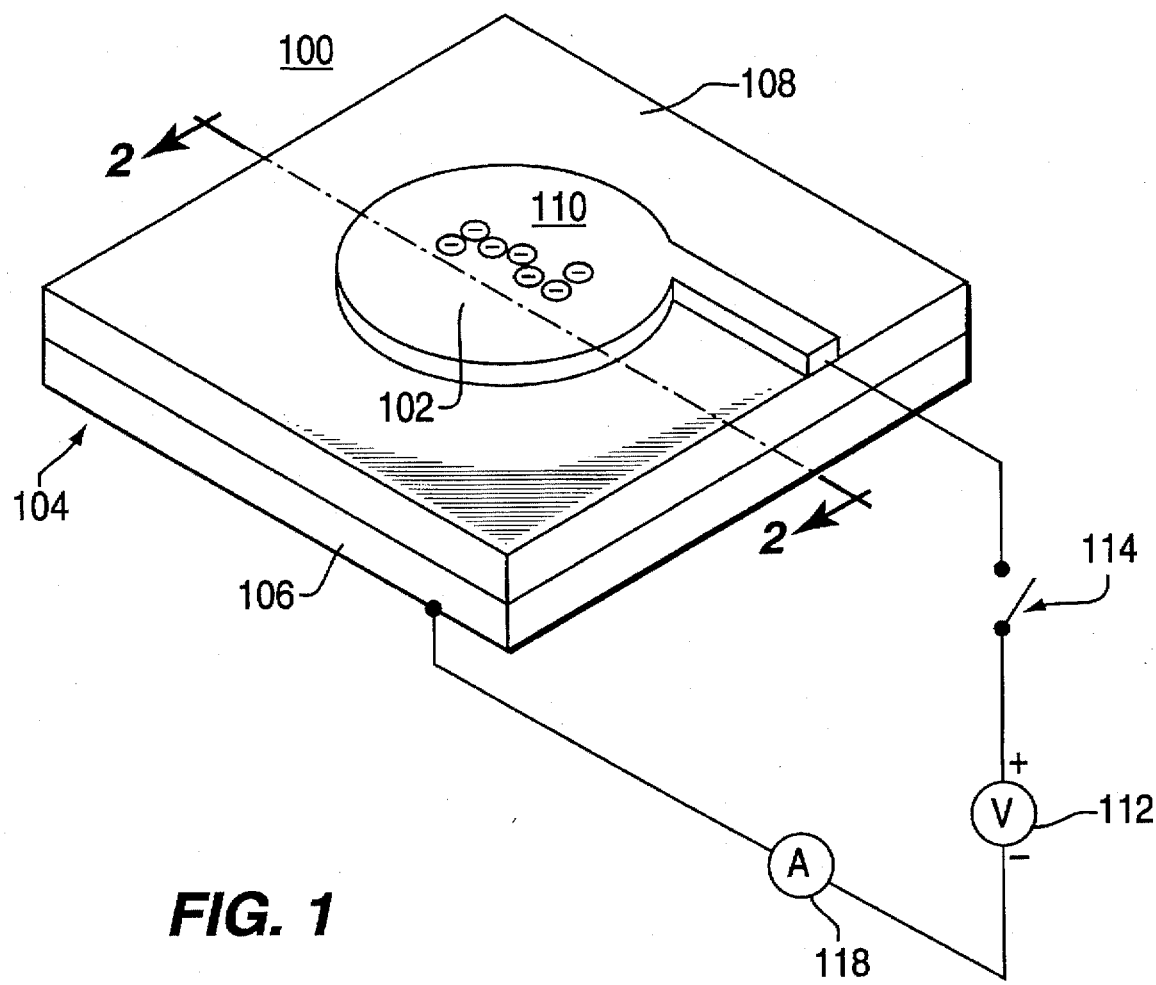
FIG. 1 depicts a perspective view of a substrate in accordance with the present invention.
Figure 2:
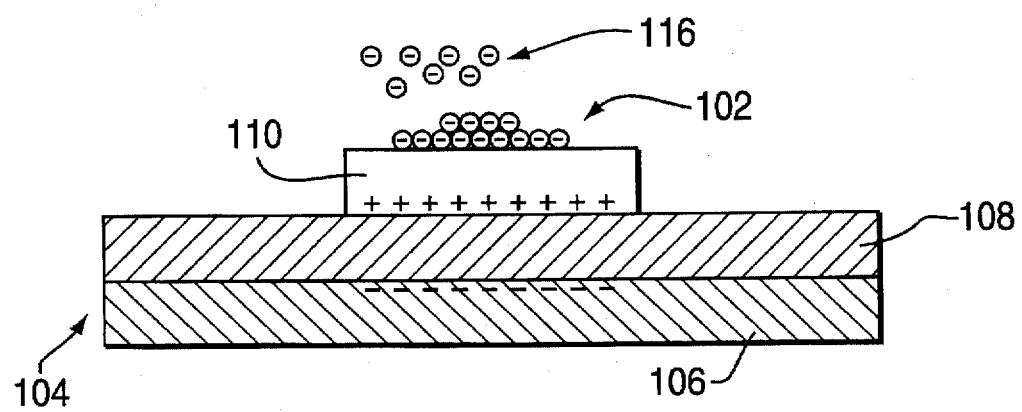
FIG. 2 depicts a cross-sectional view of the substrate of FIG. 1 taken along line 2—2.

More specifically, FIG. 1 depicts a perspective view of the invention, while FIG. 2 depicts a cross-sectional view of a substrate 104 along line 2—2 of FIG. 1. To best understand the invention, the reader should consult both FIG. 1 and 2 while reading the following detailed description of the invention.

Apparatus 100 is designed to electrostatically retain a predefined quantity of deposition material 102 within a well-defined area upon a substrate 104. The apparatus contains the substrate 104, a voltage source 112, an ammeter 118, and a switch 114. The substrate 104 contains a conductive plate 106 and a conductive trace 110 (also referred to herein as a collection trace) separated from said conductive plate by a dielectric layer 108. The dielectric layer is typically alumina of thickness 5 micrometers. The conductors are typically created using a conventional thin film deposition process.

The collection trace 110 and plate 106 have a parallel spaced-apart relation with respect to one another. One terminal of a DC voltage source 112 is connected, through switch 114, to trace 110. The other terminal of source 112 is connected through connector 118 to plate 106. By temporarily closing the switch 114, the voltage source charges the collection trace with respect to the plate. The amount of charge accumulated on the trace during a specific period of time is directly proportional to the voltage differential applied between the plate and trace, i.e., the larger the differential, the greater the accumulated charge during a given time period. Typically, the current magnitude indicated by the ammeter 118 is monitored to determine a quantity of charge accumulated on the plate during a specified period of time that the switch is closed.

Illustratively, the trace is connected to the positive terminal of the source and the negative terminal of the source (ground) is connected to the plate. As such, upon closure of the switch, the trace is charged positively with respect to the plate. Of course, the plate could be charged negatively with respect to the plate without detrimentally affecting the operation of the inventive apparatus. The voltage used to charge the trace is a relatively low voltage, i.e., the voltage is typically on the order of tens to hundreds of volts. Given a dielectric thickness of 5 micrometers and a collection trace having a diameter of 0.040 inches, the capacitance between the trace and the plate is approximately 5 pF. With such a capacitance, the time required to charge the plate is approximately 50 picoseconds. To more easily monitor the charging process, the charge duration can be increased by adding a series resistor between the plate and the voltage source.

Once a particular charge is accumulated on the trace, a deposition material 116 is disposed over the charged collection trace. The material 116 is either a powder, such as a medicament or a printing toner, or a liquid, such as a printing ink. Whether a powder or a liquid is used, the material is electrically charged before being disposed over the trace. To facilitate electrostatic attraction between the material and the trace, the charge on the material is opposite the charge on the trace.

Typically, a powder deposition material is charged using a conventional tribo-electric charging technique (e.g., using what is commonly known as a tribo-electric charging gun) that provides a substantially uniform charge-to-mass ratio on the powder particles. The powder is charged at an opposite polarity to the charge on the trace. Once charged, the powder is expelled from the tribo-electric charging gun by a flow of air or some other gas. The expelled powder forms a cloud of charged powder particles proximate the charged collection trace. The trace attracts and retains the charged powder. Assuming a substantially uniform charge-to-mass ratio on the powder particles, the amount of powder that accumulates on the trace is directly proportional to the charge density on the trace. Furthermore, the dimensions of the trace define an area in which the powder is retained. Consequently, using the invention, a particular location on a substrate retains a particular amount of powder.

On the other hand, if the material to be deposited is a liquid, the liquid is typically charged by conventional corona charging apparatus within a liquid atomizer device. The liquid is typically charged as it is atomized within the atomizer. The atomizer expels the atomized liquid proximate to the charged collection trace. The trace attracts and retains the charged liquid. As such, the particular dimensions of the trace define an area in which the liquid is retained.

In some applications of the inventive substrate, it may be necessary to coat the substrate surface, including the collection trace, with a dielectric material. Such a coating is typically required to ensure that the collection trace metal or the dielectric layer material of the substrate do not chemically react with the deposition material. A coating of this type should have little or no impact upon the operation and usefulness of the invention as described herein.

Figure 3:
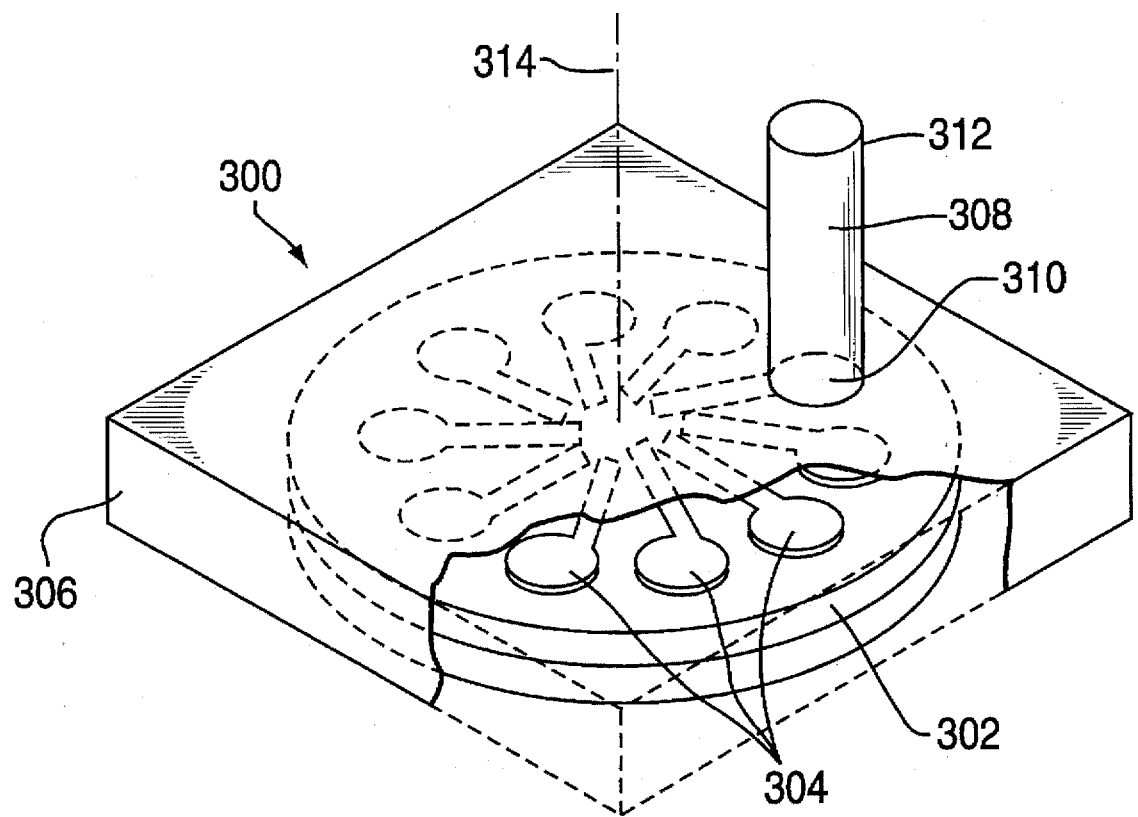
FIG. 3 depicts an illustrative application for the present invention; namely, a powdered medicament inhaler.

FIG. 3 depicts a specific application for the invention. In particular, the apparatus of FIG. 3 is a dry powder drug (medicament) inhaler 300 that is designed to retain a dry powdered drug at specific locations upon a substrate 302. As such, a powdered medicament is deposited in well defined doses in the manner discussed above and retained at particular locations upon the substrate until removed by an external force. The collection traces 304 that define the location and area upon which the medicament is retained typically have a diameter of 0.040 inches. In such an inhaler, a plurality of circular collection traces 304 are located on the substrate 302 to enable multiple doses of the medicament to be retained in well-defined locations upon a single substrate. A housing 306 encloses the substrate 302 and supports a flexible delivery tube 308. The substrate is rotatable about a central axis 314 with respect to the housing and the delivery tube. As such, the substrate can be rotated to align a particular medicament dose (i.e., a particular collection trace) with an inlet end 310 of the delivery tube 308. When a patient inhales through the outlet end 312 of the tube, the medicament is dislodged from the substrate and carried by air flow to the lungs of the patient. To promote sufficient air flow to dislodge the medicament, the substrate at each of the trace locations is perforated with a plurality of openings that are smaller than the smallest medicament particle. As such, air flows through the dose location, i.e., through perforations in the collection trace, the dielectric layer and the plate, to carry the medicament to the patient.

Figure 4:
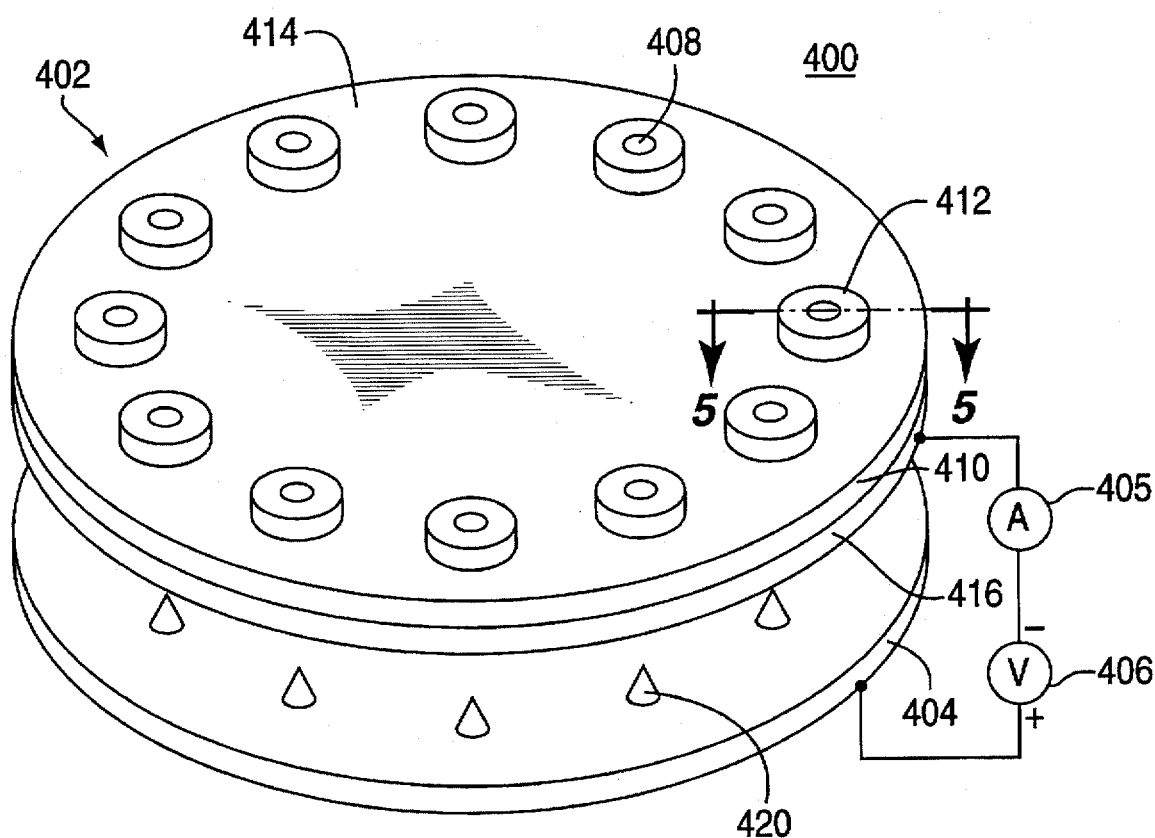
FIG. 4 depicts a substrate for use in the inhaler of FIG. 3.
Figure 5:
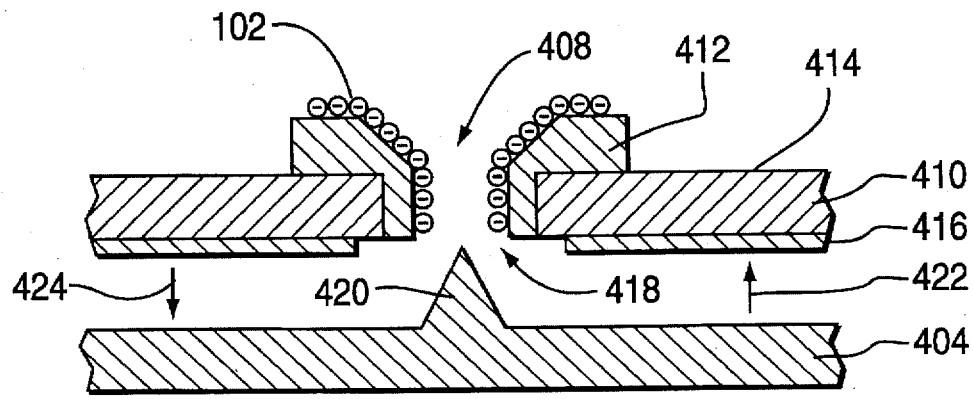
FIG. 5 depicts a cross-sectional view of an element in the substrate of FIG. 4 taken along line 5—5.
Figure 6:
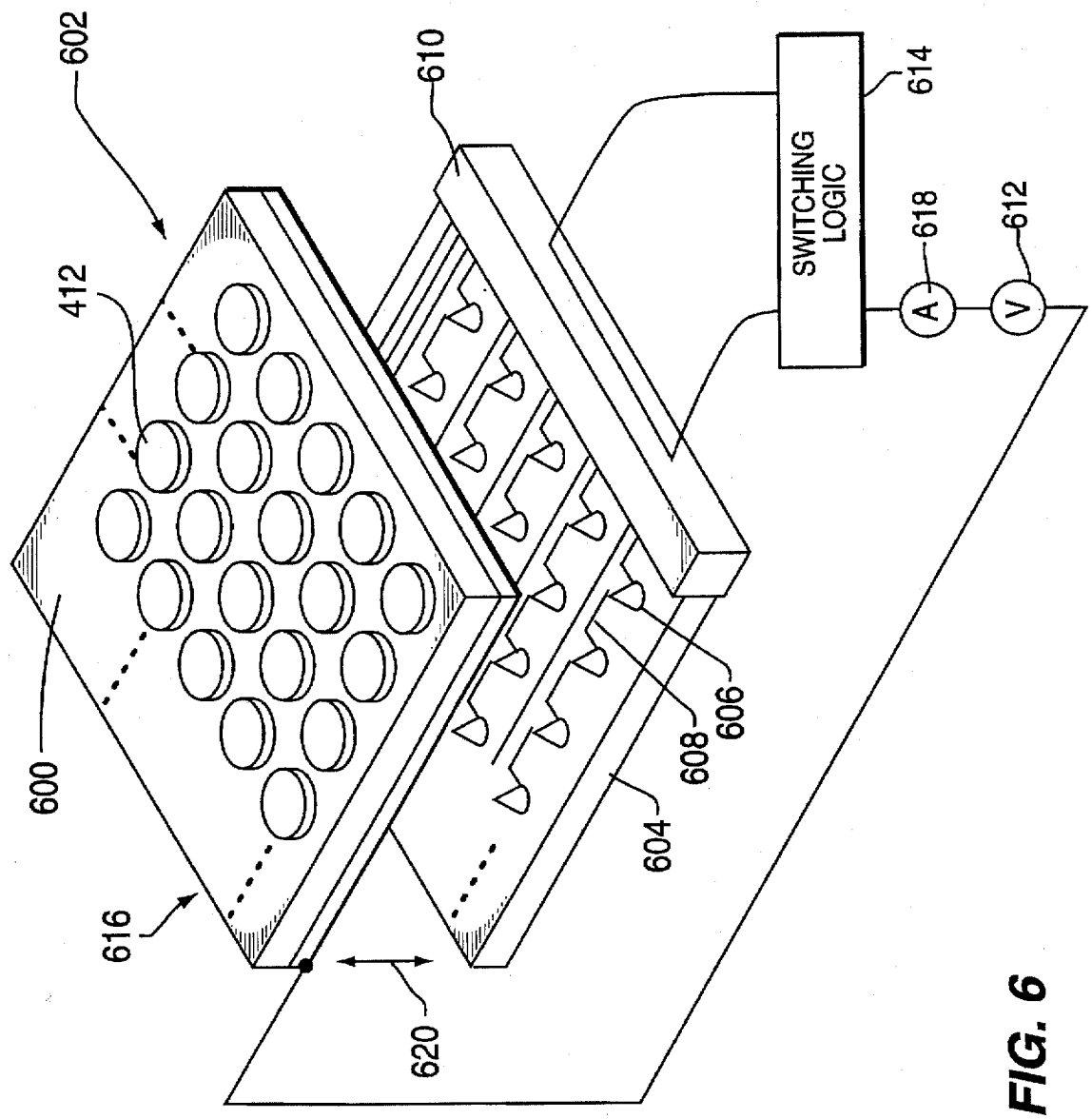
FIG. 6 depicts a second illustrative application for the present invention; namely, a programmable dot-matrix printing stamp.

FIG. 4 depicts a perspective view of another embodiment of the inventive substrate for utilization in a dry powder medicament inhaler such as the inhaler of FIG. 3. FIG. 5 depicts a cross-sectional view of the substrate in FIG. 4 taken along line 5—5. To best understand this embodiment of the invention, the reader should consult both FIGS. 4 and 5 while reading the following detailed description.

Apparatus 400 contains substrate 402, charging plate 404, an ammeter 405, and voltage source 406. Each medicament dose location contains an opening 408 through a dielectric layer 410. The opening has deposited therein a collection trace 412 that plates the surface of the opening as well as an area on a top surface 414 of the dielectric layer 410. Underlying the entire dielectric layer 414 is a conductive plate 416. The plate contains apertures 418 that are coaxial with, but slightly larger in diameter than, the openings 408 through the dielectric layer 410. Furthermore, the apparatus contains a charging plate 404 fabricated of a conductive material and having a plurality of cone-shaped protuberances 420. The protuberances are aligned with the respective openings 408 and 418 in the dielectric layer 410 and the conductive plate 416. The protuberances are sized to enter the openings 408 in the dielectric layer and contact the trace plating 412 within each opening 408 without contacting the conductive plate 416. The charging plate is connected to one terminal of a DC voltage source 406 and the conductive plate is connected through an ammeter to the other terminal of the source. As such, when a protuberance of the charging plate contacts the collection trace, a charge accumulates on the trace. Such charging is accomplished by moving the charging plate upwards in a direction indicated by arrow 422. The charge accumulated is directly proportional to the voltage applied between the trace and the conductive plate. Once a particular charge is accumulated, the charging plate is removed from contact with the collection trace by moving the charging plate downwards in a direction indicated by arrow 424.

As with the previous embodiment, to retain a medicament powder, a cloud of charged medicament is generated proximate the collection traces. By having a medicament charge that is opposite that of the trace charge, the trace retains the medicament in a quantity that is proportional to the accumulated charge on the collection trace. Thus, the location and quantity (dose) of the medicament dose is strictly controlled.

Once medicament is deposited at all the locations on the substrate, the substrate 402 is used in an inhaler such as that described with respect to FIG. 3. In this embodiment, as a patient inhales through the delivery tube, air flow passes through the opening 408 in the dielectric layer 410 and dislodges the medicament from the trace 412. The airflow carries the dislodged medicament powder to the patient's lungs.

FIG. 6 depicts another alternative embodiment of the present invention that permits each collection trace to be selectively and individually charged. Specifically, the substrate 616 contains the collection traces 412 shown in FIG. 5 arranged in an array 602 upon a dielectric layer 600. The traces for this 5 embodiment may or may not have an opening extending through the trace, i.e., the opening 408 may be filled with conductive material that comprises the collection trace 412. The charging plate 604, in the embodiment of FIG. 6, is fabricated of an insulator having a plurality of conductive protuberances 606 deposited upon its surface. The protuberances are connected to conductive traces 608 that lead to an edge connector 610 located at one edge of the charging plate. Each protuberance 606 is aligned with an associated collection trace 412 of the substrate 616.

In use, one terminal of a DC voltage source 612 is connected to the conductive plate of the substrate, while the other terminal is connected, through an ammeter 618, to selected ones of the protuberances 606. Switching logic 614 such as programmable array logic (PAL), is used to select the protuberances that are to be connected to the voltage source. Once the selection is made, the charging plate is moved upwards along arrow 620 into contact with the substrate such that each of the protuberances 606 contact their associated collection trace 412. As such, the protuberances that are selectively connected to the voltage source 612 facilitate charging of their respective collection traces.

Once charged to a predetermined charge quantity as measured on the ammeter 618, a deposition material is deposited on the collection traces. As discussed above a powder, such as a printing toner may be charged and deposited using a tribo-electric charging technique, or a liquid, such as a printing ink, can be deposited using a corona charging technique in conjunction with a liquid atomizer. In either case, the charged deposition material adheres to only those collection traces that are charged. Thus, the material adheres in a pattern defined by the collection traces that are charged. Thereafter, the traces coated with deposition material can be used in various applications such as repetitive printing onto paper or other material.

For example, if the traces are selectively coated with ink to form a dot-matrix pattern, the traces can be pressed against paper, cloth, cardboard or some other material. Absorption of the ink into the material being printed removes the ink from the collection traces. As such, the substrate forms a programmable stamp that prints in dot-matrix patterns. To facilitate release of the ink, the charging plate can be reapplied to the collection traces while all the protuberances are grounded. In this manner, the electrostatic charge is removed from the collection traces such that the ink can easily be transferred to a surface, even a non-absorptive surface.

To change the printing pattern of the programmable stamp, a user merely needs to clear the previous pattern be grounding all the collection traces and then, by altering the switching logic, redefine which of the collection traces are to be charged. Once charged, the user may redeposit the ink. This same process also works for deposition of powdered toners. However, for printing with toners, one further process step is necessary. Once the toner is deposited on a material to be printed, that material is heated to fix the toner.

Alternatively, rather than use a charging plate to charge the collection traces in any of the foregoing embodiments of the invention, the collection trace is charged using a conventional ion emitter or electron gun. As such, the emitter or gun is positioned proximate to the collection trace, activated, and, in response to bombardment by ions or electrons, the collection trace becomes charged.

Although various embodiments which incorporate the teachings of the present invention have been shown and described in detail herein, those skilled in the art can readily devise many other varied embodiments that still incorporate these teachings.

What is claimed is:

1. Apparatus for electrostatically retaining a deposition material upon a substrate, said apparatus comprising:

a dielectric layer having a first and second surface and wherein the dielectric layer defines at least one first opening;

a conductive plate disposed on the first surface of said dielectric layer, wherein the conductive plate defines a second opening that is coaxially aligned with the first opening;

a collection trace, disposed on the second surface of said dielectric layer, proximate the first opening and extending into the first opening, where said conductive plate and said collection trace have a parallel spaced-apart relation and wherein the collection trace has a first charge polarity; and a deposition material, having a second charge polarity that is opposite the first charge polarity, where said collection trace electrostatically attracts and retains said deposition material.

2. The apparatus of claim 1, wherein said deposition material is a powder.

3. The apparatus of claim 1, wherein said deposition material is a liquid.

4. The apparatus of claim 1, wherein the deposition material that is a powdered medicament, and the apparatus further comprises:

means, positioned proximate said collection trace, for extracting said powdered medicament from said collection trace.

5. The apparatus of claim 4, wherein said extracting means is a delivery tube providing for inhalation of said powdered medicament.

6. Apparatus for electrostatically retaining a deposition material upon a substrate, said apparatus comprising:
   a dielectric layer defining a plurality of first openings, the dielectric layer having a first and second surface;
   a conductive plate, disposed on the first surface of said dielectric layer, defining a plurality of second openings that are coaxially aligned with said first openings;
   a plurality of collection traces, disposed on the second surface of said dielectric layer proximate and extending into said first openings, the collection traces having a first charge polarity; and
   a deposition material, having a second charge polarity that is opposite the first charge polarity, where each of said collection traces electrostatically attracts and retains said deposition material.

7. The apparatus of claim 6, wherein each of said collection traces fill each of said openings defined by said dielectric and form a dot matrix array of printing elements.

8. The apparatus of claim 6, wherein said deposition material is a medicament powder.

9. The apparatus of claim 8, further comprising:
   means, supporting said dielectric layer, for selecting a collection trace from said plurality of collection traces;
   and means, positioned proximate said selected collection trace, for extracting said powdered medicament from said selected collection trace.

10. The apparatus of claim 9, wherein said extracting means is a delivery tube providing for inhalation of said powdered medicament.

11. Apparatus for electrostatically retaining a medicament powder upon a substrate, said apparatus comprising:
    a dielectric layer having a first and second surface;
    a conductive plate disposed on the first surface of the dielectric layer;
    a collection trace, disposed on the second surface of the dielectric layer, where the conductive plate and the collection trace have a parallel spaced-apart relation and the collection trace is disposed on the second surface of the dielectric layer, the collection trace having a first charge polarity that is retained in the absence of a voltage source; and
    a medicament powder, having a second charge polarity that is opposite the first charge polarity, wherein the collection trace electrostatically attracts and retains the medicament powder.

12. The apparatus of claim 11, wherein the dielectric layer defines at least one first opening and the collection trace is disposed on the second surface of the dielectric layer proximate the first opening and extending into the first opening, and wherein the conductive plate defines at least one second opening that is coaxially aligned with the first opening.

13. The apparatus of claim 11, further comprising an extractor for extracting the powdered medicament from the collection trace.

14. The apparatus of claim 13, wherein the extractor comprises a delivery tube providing for inhalation of the powdered medicament.

15. An apparatus for electrostatically retaining a deposition material upon a substrate, said apparatus comprising:
    a dielectric layer defining at least one first opening, the dielectric layer having a first and second surface;
    a conductive plate, disposed on the first surface of said dielectric layer, defining at least one opening that is coaxially aligned with said at least one first opening;
    at least one collection trace, disposed on the second surface of said dielectric layer proximate and extending into said at least one first opening; and
    a charging plate, for charging each of the collection traces to a first polarity, comprising at least one protuberance extending from a surface of said charging plate, each being formed to fit into a first opening to contact one of said collection traces without contacting said conductive plate, wherein the charging plate is movable between a position where the at least one protuberance contacts a collection trace and a position where the at least one protuberance does not contact a collection trace.

16. The apparatus of claim 15, wherein said conductive plate is adapted to connect with a first terminal of a voltage source and the charging plate is adapted to connect with a second terminal, of opposite polarity from the first terminal, of the voltage source.

17. The apparatus of claim 15, wherein said dielectric layer has disposed on the second surface a plurality of collection traces, and wherein said charging plate further comprises a plurality of protuberances, each of the protuberances being coaxially aligned with a respective opening defined by said dielectric layer.

18. The apparatus of claim 17, further comprising a voltage source having a first terminal connected to the conductive plate and a second terminal connected to the charging plate for charging the collection traces at the first charge polarity.

19. The apparatus of claim 18, wherein said voltage source is connected to said conductive plate and said collection trace through an ammeter.

20. The apparatus of claim 18, further comprising a switch means, connected between said voltage source and said collection trace, for controlling the quantity of charge accumulated on said collection trace.

21. The apparatus of claim 18, further comprising switching logic, connected between said voltage source and said charging plate, for selecting specific ones of said protuberances for connection to said voltage source.

22. The apparatus of claim 21, wherein said deposition material is printable substance.

* * * * *